(12) United States Patent
Gibson et al.

(10) Patent No.: US 8,264,219 B2
(45) Date of Patent: Sep. 11, 2012

(54) IN-LINE PIPE INSPECTION TOOL

(75) Inventors: Michael Gibson, Newcastle (GB);
Christopher Envy, Newcastle (GB);
Paul Mundell, Newcastle (GB)

(73) Assignee: PII Limited, Cramlington (GB)

( * ) Notice: Subject to any disclaimer, the term of this patent is extended or adjusted under 35 U.S.C. 154(b) by 0 days.

(21) Appl. No.: 12/842,086

(22) Filed: Jul. 23, 2010

(65) Prior Publication Data

US 2010/0308810 A1   Dec. 9, 2010

Related U.S. Application Data

(62) Division of application No. 11/571,451, filed as application No. PCT/GB2005/002426 on Jun. 20, 2005, now Pat. No. 7,784,368.

(30) Foreign Application Priority Data

Jun. 30, 2004  (GB) .................. 0414672.6

(51) Int. Cl.
*G01N 27/82* (2006.01)
*G01R 33/12* (2006.01)

(52) U.S. Cl. ........ 324/220; 324/240; 324/262; 73/865.8

(58) Field of Classification Search .................. 324/219, 324/220, 240, 242, 262; 73/865.8
See application file for complete search history.

(56) References Cited

U.S. PATENT DOCUMENTS

| | | | |
|---|---|---|---|
| 3,978,939 A | 9/1976 | Trouiller | |
| 4,055,824 A * | 10/1977 | Baermann | 335/288 |
| 4,876,672 A | 10/1989 | Petermann et al. | |
| 6,538,431 B2 | 3/2003 | Couchman et al. | |
| 6,762,602 B1 | 7/2004 | Laursen et al. | |
| 6,904,818 B2 | 6/2005 | Harthorn et al. | |
| 6,944,902 B1 | 9/2005 | Richter et al. | |

FOREIGN PATENT DOCUMENTS

| | | |
|---|---|---|
| EP | 0083759 A2 | 7/1983 |
| EP | 0654631 A1 | 5/1995 |
| EP | 1486755 A2 | 12/2004 |
| GB | 2011004 A | 7/1979 |

* cited by examiner

*Primary Examiner* — Reena Aurora
(74) *Attorney, Agent, or Firm* — Potomac Patent Group PLLC

(57) ABSTRACT

An in-line pipe inspection tool has one or more inspection platforms (28, 30) which are connected to an elongate wheeled trolley by link arms (20 to 26). The trolley unit (10, 12) has drive means for driving the point of connection of the first link arm (20, 22) to the trolley (10) relative to the point of connection of the second link arm (24, 26) to the trolley (12), thereby to move the inspection platforms (28, 30) in a direction perpendicular to the direction of elongation of the trolley (10, 12). Thus the inspection platforms (28, 30) are movable which is relative to the trolley (10, 12) to permit the tool to be adapted to pipelines of different diameters. Moreover, the platforms (28, 30) preferably have permanent magnets which contain a rotatable magnet. The rotatable magnet permits the net magnetic field generated by the platform to be varied.

20 Claims, 13 Drawing Sheets

IN-LINE PIPE INSPECTION TOOL

BACKGROUND OF THE INVENTION

1. Field of the Invention

The present invention relates to an in-line pipe inspection tool, also known as a pipeline pig.

2. Summary of the Prior Art

It is known to inspect the inside of a pipeline using a pipeline pig which passes down the pipe. For magnetic inspection, the pig has permanent magnets defining first and second pole pieces, which are positioned adjacent the inner wall of the pipe. Those magnets then generate magnetic fields which magnetise the wall of the pipe. Sensors are provided between the magnetic poles, which detect the magnetic flux density at the internal surface of the pipe. The magnetic field in the pipe wall is normally constant, but is disturbed by a flux changing feature, such as a defect, weld bead or wall thickness change, and magnetic flux then leaks out of the pipe at such a feature, to be detected by the sensors. As the pipeline pig is driven along the pipe, the location of the pole pieces, and the sensors, moves along the pipe enabling the internal surface of the pipe to be inspected.

In most pipeline pigs, the pole pieces extend cylindrically around the pig, to define a fixed structure. However, such an arrangement has the problem that it cannot then adapt to pipelines of different diameters, and to other features of pipeline such as mitred bends, valves, etc.

Therefore, it has been proposed to mount the pole pieces, sensors, etc on an inspection platform which is connected to the rest of the pig by a variable linkage. An example of such a pig is disclosed in U.S. Pat. No. 6,538,431. In that document, a pipeline pig has a central body member with inspection platforms connected thereto by links which have carrier members on the central body, which carrier members are axially slideable along the body, and which sliding is resisted by springs. The springs thus bias the carrier members to a predetermined position, and the linkage then holds the inspection platforms with a predetermined spacing from the central body. However, if inward radial pressure is applied to the inspection platforms, e.g. because of a reduction in the diameter of the pipe, the carrier members are pushed against the resistance of the springs thereby permitting the shape of the linkage to change, and to permit the inspection platform to move inwardly.

Thus, U.S. Pat. No. 6,538,431 proposes passive movement of the inspection platforms. Since the inspection platforms must make contact with the pipe wall (both as part of their inspection function but also when they are to be moved radially), U.S. Pat. No. 6,538,431 also proposed that the inspection platforms have bristles thereon, to act as magnetic coupling between the pole pieces and the pipe wall, and also to provide a contact for the inward radial force to be applied.

However, the use of such bristles has the disadvantages that they cause friction between the inspection platform and the wall of the pipe, thereby requiring a high force to move the pipeline pig along the pipe.

SUMMARY OF THE INVENTION

Therefore, as its most general, the present invention proposes that the linkage between the inspection platform or platforms and the central body member be a powered connection, in which the linkage is driven to change shape, and thus to move the inspection platform(s) radially relative to the central body.

Moreover, in the present invention, the central body is a trolley having wheels which will roll along the internal surface of the pipe.

Thus, according to the first aspect of the present invention there may be provided an in-line pipe inspection tool comprising
an elongate wheeled trolley unit;
an inspection platform;
first and second link arms each connected between the inspection platform and the trolley, the points of connection of the link arms to the platform being spaced apart;
wherein the trolley unit has drive means for driving the point of connection of the first link arm to the trolley relative to the point of connection of the second link arm to the trolley, thereby to move the inspection platforms in a direction perpendicular to the direction of elongation of the trolley.

It should be noted that the present invention is not limited to an in-line pipe inspection tool in which the inspection platform carries one or more magnetic sensors, although this is one use for the present invention. The present invention may be applied to in-line pipe inspection tools of other types. These may include, but are not limited to, tools using ultrasonic transducers, electro-magnetic acoustic transducers or pulsed eddycurrent sensors, which sensors may then be carried on the inspection platform of the invention as defined above.

There are many different arrangements, within the present invention, for driving the points of connection of the link arms to the trolley to vary their spacing. For example, the link arms may terminate at connection members on the trolley, and one or both of those connection members may be connected to a motor driven worm screw or to a hydraulic ram, which changes the position of one connection member relative to the other, on the trolley. Alternatively, the trolley may comprise first and second motor units connected by a spring. The link arms then terminate in connection members attached to respective motor units, and are interconnected by the spring. Then, if the motor unit drives a wheel to cause it to move towards, or away from, the other motor unit the separation of the connection members will change, thereby moving the inspection platform radially. Thus, in this latter arrangement, the wheels of the trolley not only act as supports for the inspection tool, but also to permit movement of the connection members relative to each other.

It should be noted that, in any of these alternatives, there may also be one or more traction units connected to the inspection tool, to drive it along the pipe. Alternatively, or in addition, pressure arrangements may be used in which the force of gas in the pipeline pushes the tool along the pipe due to e.g. a pressure plate on the tool which bears against the inner wall of the pipe to enable a pressure differential across it.

The wheels of the trolley may be provided at one side of a central member, but in that case it is important that the tool maintains an orientation with those wheels at the bottom thereof, so that they support and centralise the pig. Otherwise, if the pig were to rotate in the pipe, the wheels could fail to support the pig and the pig would then be supported only by the inspection platform(s), which would be undesirable. Therefore, it is possible for wheels to be provided at more than one circumferential position, so that the wheels will bear against the pipe in respect of the orientations of the pig. However in such circumstances it is desirable that the radial separation of the wheels is variable, again to adjust to pipes of different diameter.

Preferably, the or each inspection platform is curved in the circumferential direction. In that way, it can conform, at least to some extent, to the internal surface of the pipe.

Preferably, the tool has two inspection platforms, positioned on radially opposite side of the trolley.

At least one, preferably all the link arms may contain means (e.g. spring loading) permitting resilient deformation of the link in the direction of the extension of the link. This resilience provides a degree of movement to the platform(s) to allow for compliance at bends or dents in the pipe.

Preferably the trolley is articulated. For example the motor units referred to previously may be connected to the trolley by a hinged link. Alternatively, or in addition, the wheels may be mounted on units which are hinged to a central trolley part. This is of particular importance where wheels are provided which have a variable radial separation. The structure needed to provide such a variable separation may contribute to an increase in the overall length of the trolley, increasing the desirability of articulation.

Where the wheels have a variable radial separation it is desirable for that variation to be linked to the movement of the platform(s), so that the radial movement of the platform(s) and the radial movement of the wheels occurs at the same time and the variation is proportional. The variation does not have to have the same magnitude, and indeed it may be preferable for the wheels to move a different distance than the platform(s). However, the degree movement of the wheels and platform(s) should desirably be related. This may be achieved by mounting the wheels on link assemblies which are directly connected to points of attachment of the first and second link arms to the trolley, e.g. via a bracket, so that relative movement of those attachment points varies the configuration of the link assemblies, thereby moving the wheels.

It has been found with this invention that a pipeline pig can be manufactured that can be used in a pipeline with a configuration that would otherwise make it unsuitable for inspection with a conventional pig, such as because it contains e.g. 90° mitred bends, and/or plug valves. Such valves have openings considerably less than the diameter of the pipe, and sometimes the openings are rectangular in shape. Thus, the pig can be configured so that it can pass through such a valve, and then re-expand to bring the inspection platforms back into close proximity to the internal wall of the pipe. This then allows inspection on both sides of the valve or other obstacle, and possibly inspection inside the obstacle itself.

A second aspect of the present invention is concerned with the structure of the inspection platform for inspecting the pipe. It is particularly concerned with the way the magnetic fields are controlled in such an inspection platform.

As has been discussed previously, a conventional pipeline pig has a cylindrical body which lies coaxially of the pipe with its surface just within the inner surface of the pipe. Part of the pig is arranged to generate a strong magnetic field which magnetises the wall of the pipe. The magnetic field thus generated is monitored with an array of sensors mounted on the pig which detect the magnetic flux density at the internal surface of the pipe. The magnetic field in the pipe wall is normally constant, but is disturbed by a flux changing feature, such as a defect, weld bead or wall thickness change, and magnetic flux leaks out of the pipe to be detected by the sensors.

Normally, the magnets of the pig are coupled to the wall of the pipe through mild steel bristles which contact the pipe wall. However, the bristles cause drag on the movement of the pig.

Moreover, as previously discussed, the present invention is concerned with the inspection of pipes of non-standard configurations, and the inspection platforms described above may then be unsuitable.

For example, if the pig must pass through sections of pipe of different diameter, the use of a cylindrical platform which conforms to the internal wall of the pipe is clearly unsuitable. If it is made to conform to the smaller part of the pipe, it will be spaced too far from the wall of the pipe in the larger pipe part. If, on the other hand, it conforms to the larger pipe part, then it will not be able to fit into the smaller pipe part.

The first aspect of the invention therefore included the feature that the pig (inspection tool) had at least one, preferably a plurality, of inspection platforms which could be moved radially relative to the axis of the pipe, so be moved to a position close to the wall of the pipe, or moved away therefrom at, e.g. a change in pipe diameter, corner, or other feature. Thus, in the first aspect, the platform may be a curved body having one or more permanent magnets defining north and south poles, and sensors mounted between those poles which are able to monitor the field and flux leakage at the internal surface of the pipe wall, at the location of the platform.

However, it has also been found that it is necessary to vary the magnetic field generated by the permanent magnets. Otherwise, there is a risk of a platform or platforms over-saturating or clamping to the pipe wall, during times of, for example, launch, deployment or retrieval, or where there is a change in the configuration of the pipe.

Therefore, it has been realised that there is a need to permit the magnetic field generated by the platform in the wall of the pipe to be reduced at appropriate times.

Therefore, at its most general, a second aspect of the present invention proposes that at least one, preferably both, of the permanent magnets of the or each inspection platform contains within it a rotatable magnet.

The or each permanent magnet will have a direction of magnetisation, as will the rotatable magnet. However, the fact that the rotatable magnet can be turned relative to the permanent magnet means that its direction of magnetisation can be positioned so that it is aligned in parallel with the direction of magnetisation of the permanent magnet, or aligned in anti-parallel or at some intermediate angle. In the parallel state, its magnetic flux adds to the magnetic flux of the pole piece, generating a maximum magnetic field. In the anti-parallel arrangement the flux due to the rotatable magnet is in direct opposition to the flux of the permanent magnet, so the net flux is reduced, as compared with the parallel position. Thus, the rotatable magnet may be used to minimise the magnetic output of the permanent magnet, thereby reducing its clamping effects to such levels to make it more readily detachable from the pipe wall. Where the aim is to minimise the output of the permanent magnet, it is preferable that the rotatable magnet is lined in anti-parallel with the permanent magnet.

However, it is also possible to use the rotation of the rotatable magnet to provide control of the magnetic field in the pipe wall.

The magnetic field in the pipe wall is dependent on the wall thickness. If the permanent magnet is designed to provide an adequate field for inspection in a thicker walled pipe, then the field in a thin walled pipe will be considerably higher. Whilst this does not prevent inspection of such a thin walled pipe, control of the pipe wall field may permit more accurate inspection to be achieved. For example, if the dynamic range of the electronic circuitry controlling the sensors is limited, an excessive field can result in electronic saturation or "clipping" of the signals of the electronic circuit. Thus, by controlling the field to be lower in a thin walled pipe, it is possible to ensure that all signals are within the dynamic range of the circuitory.

Secondly, pipe steel exhibits magnetic hysteresis. That is, the magnetisation level in the steel is not uniquely dependent on the applied field, and can be dual valued at any field depending on whether the field is increasing or decreasing. This would be apparent in an bi-directional operation where the tool travels out and back. The pipe would be magnetised in one direction on the way out, and in the opposite direction on the way back. Although the effect is usually small, it can introduce a small error in the defect sizing accuracy. Control of the field permits compensation for the "magnetic history" effects, and thus enables sizing accuracy to be improved.

Thirdly, although most tools run at high field in order to magnetically saturate the pipe wall, data obtained at low to medium fields can provide additional information concerning material effects brought about by mechanical damage to the pipeline. Control of the field would enable multiple passes to be made at two or more applied field levels, to enable other pipeline defect features to be characterised.

In order to control the field, it is proposed that the rotatable magnets can be positioned at an intermediate angle. This only partly cancels or attenuates the flux output and the field in the pipe wall. The sensors on the platform are continually measuring the field at the surface of the pipe wall, and can be used to provide the information necessary for controlling the angle of rotation. The rotatable magnets may then be set in an intermediate position which reduces the flux output across the pole face of the magnet. Other angular positions or orientations are possible.

Preferably, the rotatable magnet is a cylinder mounted in a bore in the permanent magnet pole piece and is rotatable in that bore.

The result can be considered to be a magnetic shunt which the rotatable magnet either contributes to, or attenuates, the effect of the permanent magnet of the pole piece.

As is described above, the inspection platform can comprise a pair of permanent magnets, either or both of which contains one or more rotating shunt magnet, together with an array of sensors between those permanent magnets.

In practice, it may be desirable for the platform to comprise a plurality of platform units, each comprising the pole pieces, shunt magnets and sensors. Such platform units will be referred to as magnetising shoes.

It is then desirable for the shoes to be connected by a flexible joint, to permit the curvature of the platform to be varied by flexing the shoes relative to each other. This means that although the pole pieces have a fixed curvature, the curvature of the platform as a whole may be varied. The degree of flexure permitted will normally be set by the maximum and minimum pipe diameters likely to be encountered by the platform.

Although envisaged for use with the first aspect of the present invention, the second aspect may be used independently on a pipeline pig, and so represents an independent aspect of the present invention.

When combined with the first aspect, the second aspect may be incorporated in any or all of the platforms of the pig.

BRIEF DESCRIPTION OF THE DRAWINGS

Embodiments of the present invention will now be described in detail, by way of example, with reference to the accompanying drawings, in which.

DETAILED DESCRIPTION

Figure 1:
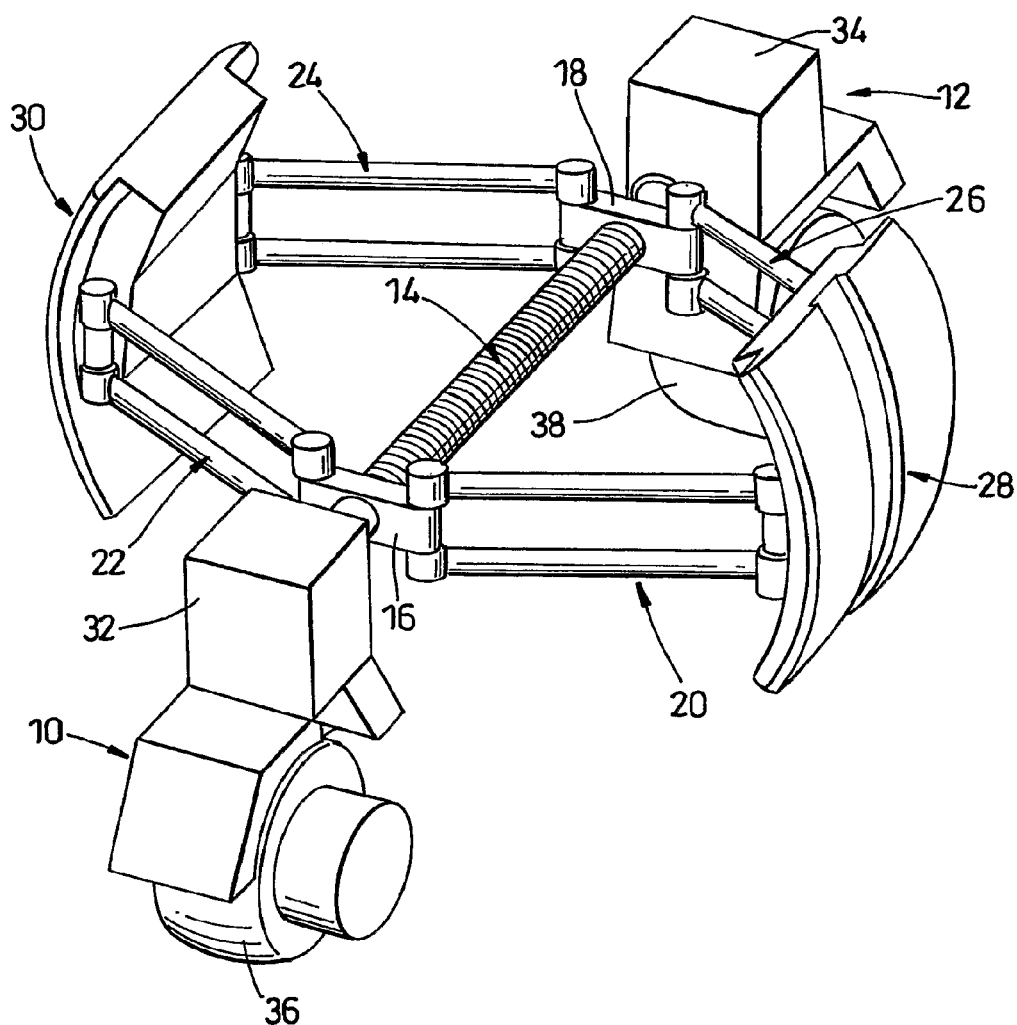
FIG. 1 is a schematic view of a first embodiment of the present invention.

A first embodiment of the present invention is illustrated in FIG. 1. In the embodiment of FIG. 1, a trolley unit is formed by first and second wheel units 10, 12 interconnected by a central spring 14. The spring 14 is such as to tend to pull the wheel units 10, 12 towards each other to a distance determined by the minimum extension of the spring. Each wheel unit 10, 12 has a bracket 16, 18 thereon, and each bracket 16, 18 has a pair of link arms 20 to 26 extending there from in opposite directions. A link arm 20, 26 from each bracket 16, 18 is connected to a first inspection platform 28, and the other link arms 22, 24 are connected to a second inspection platform 30. The connection of the link arms 20 to 26 to their respective brackets 16, 18 and inspection platforms 28, 30 are hinged to permit the angle of the link arms 20 to 26 relative to the spring 14 to be varied. Moreover, the link arms 20 to 26 or their mountings may be sprung loaded to provide a measure of compliance at dents and bends in the pipe.

As can be seen from FIG. 1, the link arms 20 to 26 each comprise a pair of links forming a parallel arrangement, since this resists movement of the inspection platforms 28, 30 in the circumferential direction. The detailed structure of the inspection platforms will be discussed in more detail later.

Each wheel unit 10, 12 has a motor 32, 34 which drives a corresponding wheel 36, 38. When the inspection platforms 28, 30 are deployed to inspect the interior of a pipeline, the spring 14 draws the wheel units 10, 12 towards each other, thereby forcing the inspection platforms 28, 30 outwardly towards the wall of the pipe. When, however, the inspection platforms 28, 30 need to be retracted to conform to a narrower pipe, mitered bend or plug valve, the motors 32, 34 drive the wheels 36, 38 to move the wheel units 10, 12 apart, against the force of the spring. This moves the brackets 16, 18 apart, thereby pivoting the link arms 20 to 26 such that the spacing in the radial direction in between the spring 14 and the inspection platforms 28, 30 is reduced. The wheel units can be driven to whatever separation is necessary to retract the inspection platforms 28, 30 to a sufficient degree. In a modification of the embodiment of FIG. 1, the wheel units 10, 12 may be replaced by respective tractor units, the trolley unit of the present invention then being formed by those tractor units, the spring 14, and the brackets 16, 18.

The potential disadvantage of embodiment of FIG. 1 is that the wheels 36, 38 will support the tool only when they are lowermost. Since this cannot be guaranteed as the pig moves along the pipe, it is possible for the tool to adopt orientations in which the platforms 28, 30 are one above the other, so that the upper one depends on the tension in the spring for it to be supported in place.

There is then a risk that the upper platform could come away from the pipe wall, compromising its operation. Similar problems occur in other positions.

Figure 2:
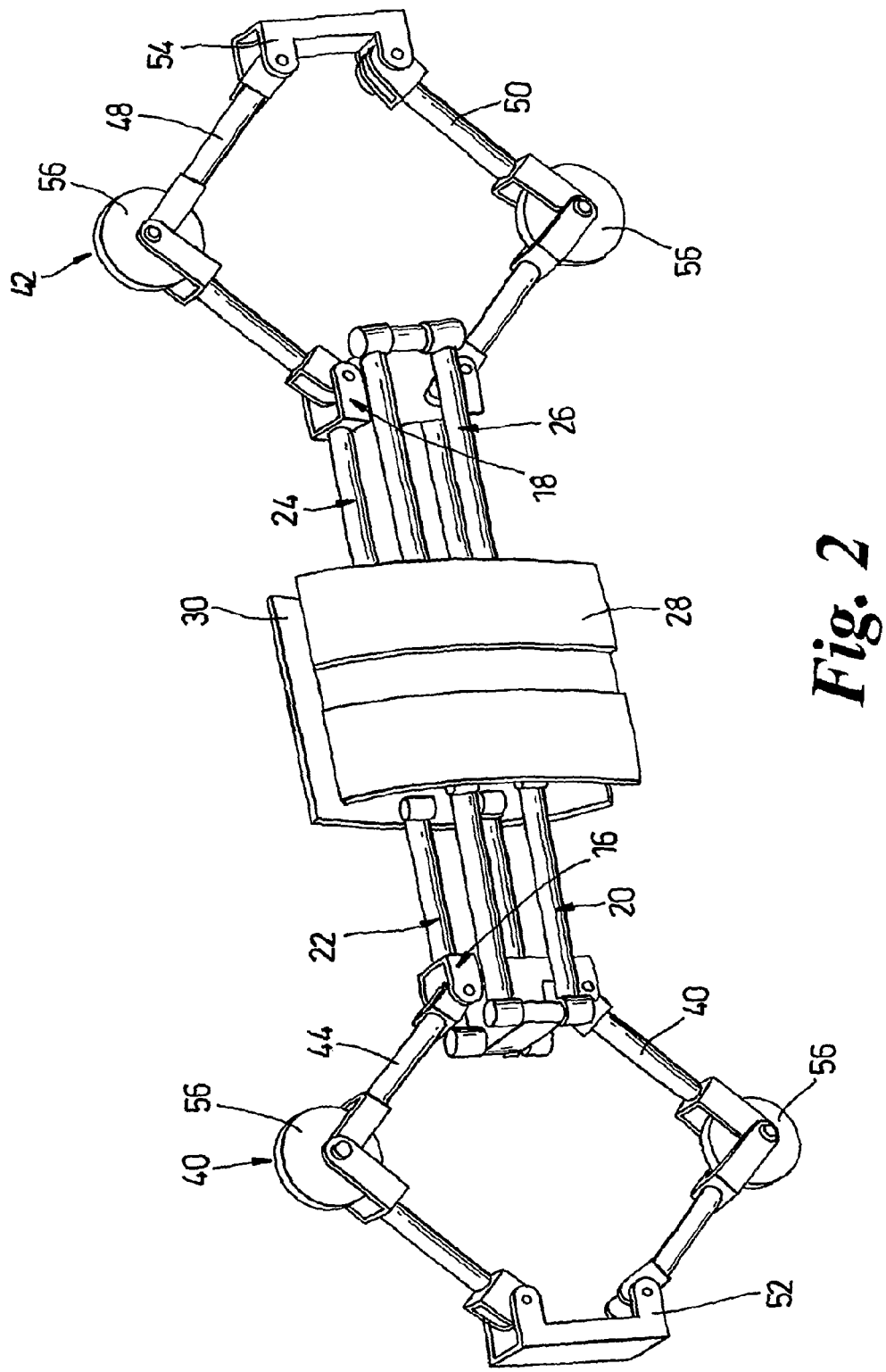
FIG. 2 is a schematic view of a second embodiment of the present invention, in a first position.

Therefore, it may be desirable to centralise the tool within the pipe. The embodiment of FIG. 2 illustrates an arrangement for achieving this. Note that some parts of the embodiment of FIG. 2 correspond to those of FIG. 1, and are indicated by the same reference numerals.

In the embodiment of FIG. 2, centralising units 40, 42 are provided between the brackets 16, 18 and the wheel units (which are not shown in FIG. 2). As previously, those wheel units may be replaced by tractor units.

Each centralising unit 40, 42 has a parallelogram arrangement of arms of fixed length, defining upper and lower V-shaped links 44, 46, 48, 50 between the brackets 16, 18 and further brackets 52, 54 to which of the motor units are connected. At the middle of each V-shaped link 44 to 50 is a corresponding wheel 56.

In the position shown in FIG. 2, in which the inspection platforms 28, 30 are retracted, the V-shaped links 44 to 50 are positioned so that the wheels 56 will be in contact with the inner surface of the pipe. It may be necessary to provide additional tension or compression springs to maintain the centralising units 40, 42 in the appropriate position.

Figure 3:
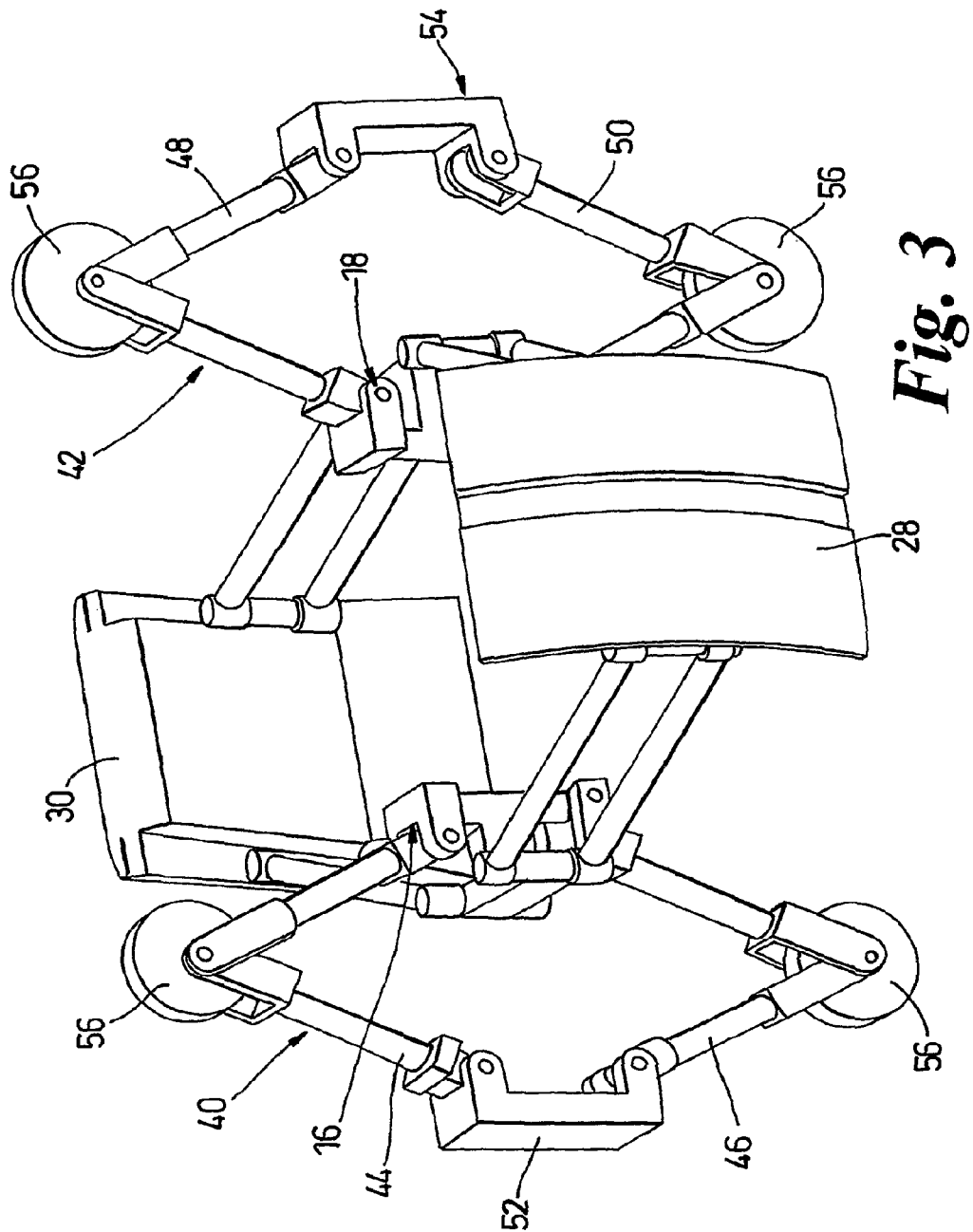
FIG. 3 shows the embodiment of FIG. 2, in a second position.

FIG. 3 illustrates the second embodiment, but with the platforms 28, 30 deployed. It can be seen that not only are the brackets 16, 18 are closer together, to deploy the inspection platforms 28, 30, but the bracket is closer to the bracket 16, and the bracket 54 is closer to the bracket 18, thereby decreasing the angle between the arms of the V-shaped links 44 to 50 of the centralising units, moving the wheel 56 outwardly so that they maintain contact with the inner wall of the pipe.

Thus, the centralising units 40, 42 causes the central axis of the tool (along which the spring 14 runs) to be on the centre line of the pipe. This counters any sagging of the tool.

Preferably, the centralising units 40, 42 are pivotally connected to the brackets 16, 18 to permit the pivoting of centralising units 40, 42 about an axis parallel to the plane of the V-shaped links 44 to 50. This allows articulation of the tool, e.g. at bends in the pipe.

One disadvantage of the embodiment of FIGS. 2 and 3 is that the overall length of the tool is increased by the centralising units 40, 42 and this may cause problems if the tool were to encounter a miter joint in a narrow pipe. The embodiment of FIG. 1 would then be preferable. The choice of tool configuration may then depend on the configuration of the pipe to be inspected.

In the first and second embodiments, the deployment and retraction of the inspection platforms 28, 30 is controlled by the effect of the motor units 10, 12 and the spring. In the embodiments now to be described, powered arrangements are provided since they may allow more accurate positioning of the inspection platforms 28, 30. Again, however, corresponding parts will be indicated by the same reference numerals.

Figure 4:
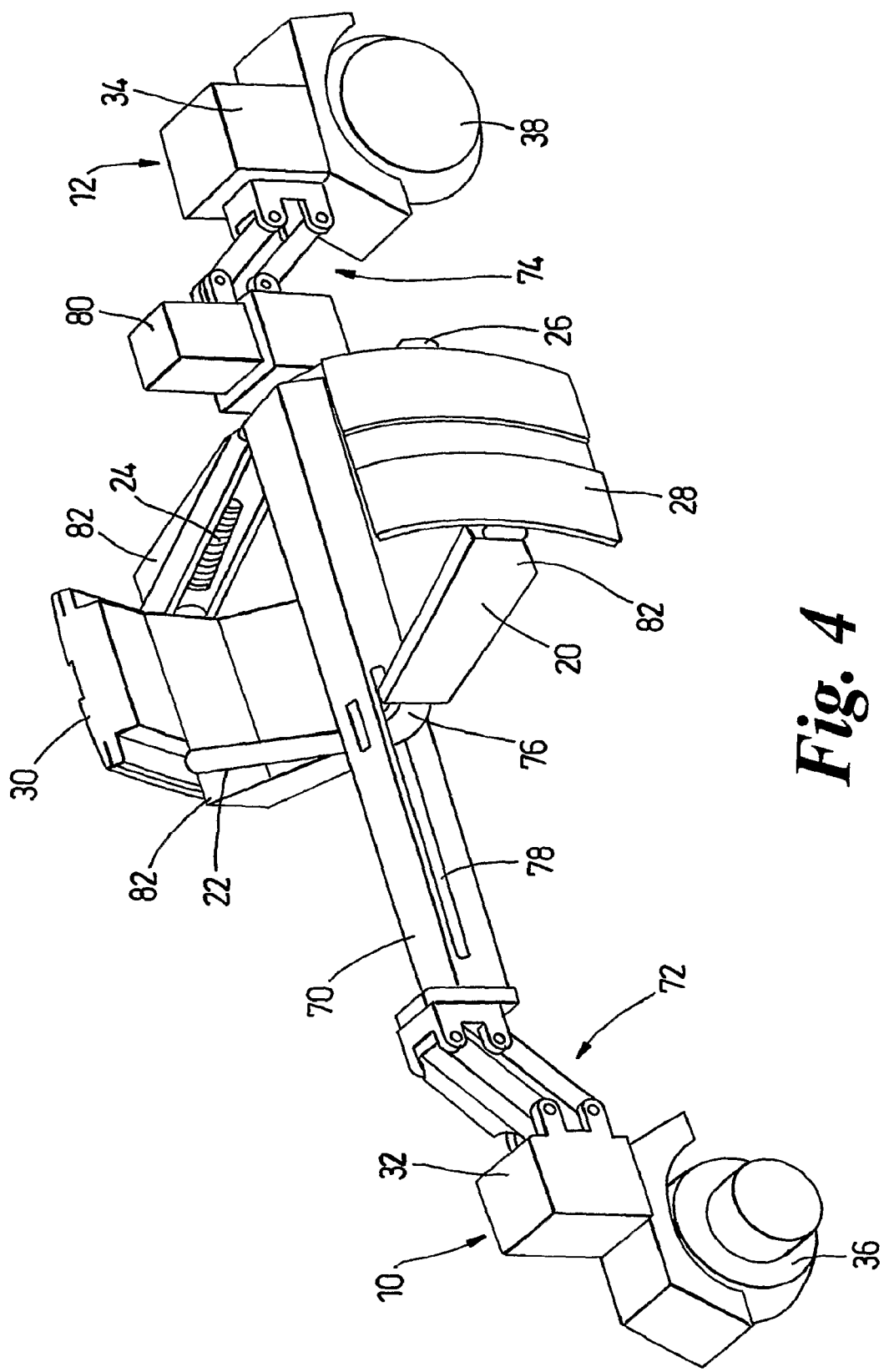
FIG. 4 shows a third embodiment of the present invention, in a first position.
Figure 5:
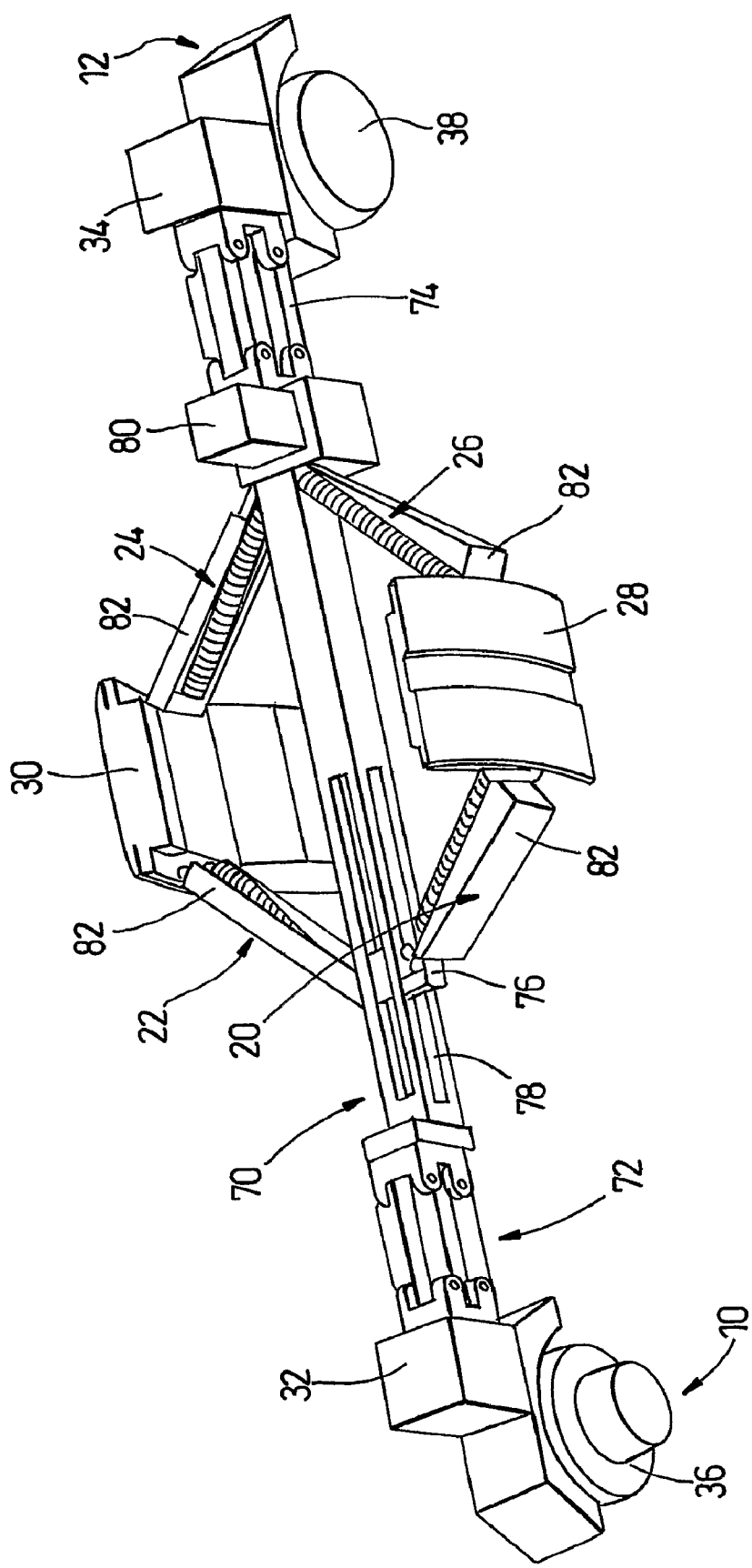
FIG. 5 shows the third embodiment of the present invention, in a second position.
Figure 6:
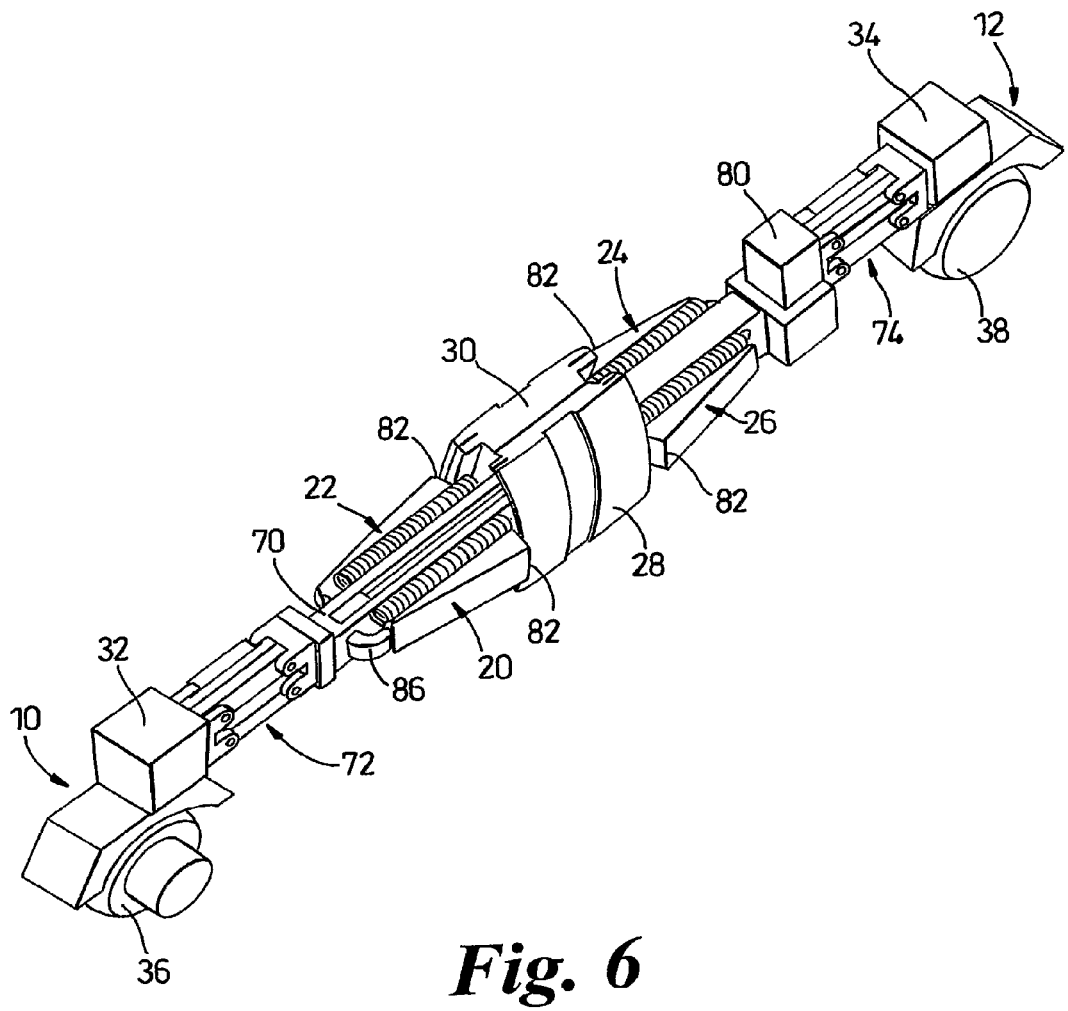
FIG. 6 shows the third embodiment of the present invention, in a third position.

Thus, in the third embodiment illustrated in FIGS. 4 to 6 the trolley has a central rigid link 70, connected to the wheel units 10, 12 by articulated links 72, 74. Although the link arms 24 and 26 are connected to that central link by pivoting connections, the point of pivoting is fixed. The link arms 20, 22 are then connected at their ends remote from the inspection platforms 28, 30 to a block 76 which is slideably mounted in a slot 78 in the central link 70. The block 76 is connected to a worm screw extending within the central link 70 and driven by a motor 80.

FIG. 4 then illustrates the configuration of the tool in which the inspection platforms 28, 30 are fully deployed. The block 76 is at one end of the slot 78 closest to the motor 80, so that the spacing between that block 76 and the connection of the link arms 24, 26 to the central link 70 is as small as possible. FIG. 5 then illustrates a partially retracted position, in which the motor 80 drives the block 76 leftwardly in FIGS. 4 and 5, thereby increasing the separation of the block 76 and the mounting point of the link arms 24, 26 on the central link 70, thereby retracting the inspection platforms 28, 30. FIG. 6 then illustrates the fully retracted position, in which the motor 80 drives the block 76 to the end of the slot 78 remote from the motor 80, so that the link arms 20 to 26 are brought as close as possible to the central link 70.

Thus, in this third embodiment, the deployment of the platforms 28, 30 no longer relies on a push/pull effect from the motor units 10, 12 (or driven trolleys). Instead, the motor 80, and the worm screw driven thereby, provides the appropriate positioning of the inspection platforms 28, 30.

As was mentioned previously, the central link 70 is connected to the motor units 10, 12 by respective link mechanisms 70, 72. These link mechanisms provide centralisation of the central link within the pipe. Each link mechanism 72, 74 comprises a pair of parallel arms pivotally connected respective ends to the central link 70 and the motor units 10, 12. Thus, if the motor units 10, 12 are driven towards each other, and since the length of the central link 70 is fixed, the link mechanism 72, 74 will pivot to move the central unit 70 upwards relative to the wheels 36, 38, as shown in FIG. 4. Similarly, if the wheel units 10, 12 are driven apart, the link mechanism 72, 74 will tend to align with the central link 70, as illustrated in FIGS. 5 and 6. Thus, by controlling the relative position of the motor units 10, 12, the position of the central link, and hence the inspection platforms 28, 30 within the pipe, can be adjusted.

FIGS. 4 to 6 also illustrate that the link arms 20, 22, 24 and 26 may have protective deflectors 82 thereon. The deflectors 82 are wedge-shaped, tapering in a direction away from the platforms 28, 30. The deflectors 82 act as guides when an obstacle is encountered, to prevent edges of that obstacle striking the platforms 28, 30 which could damage them.

Figure 7:
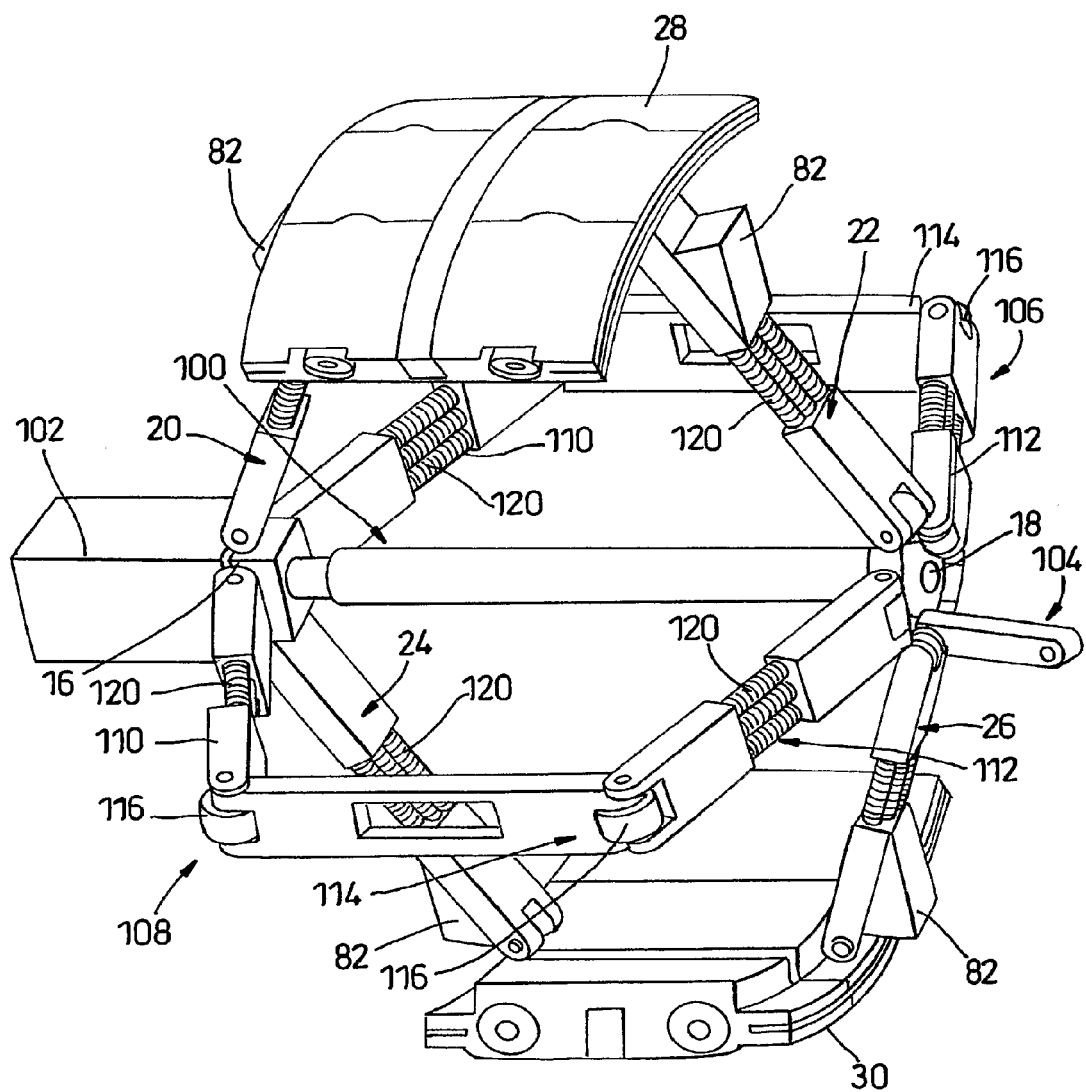
FIG. 7 shows a fourth embodiment of the present invention, in a first position.
Figure 8:
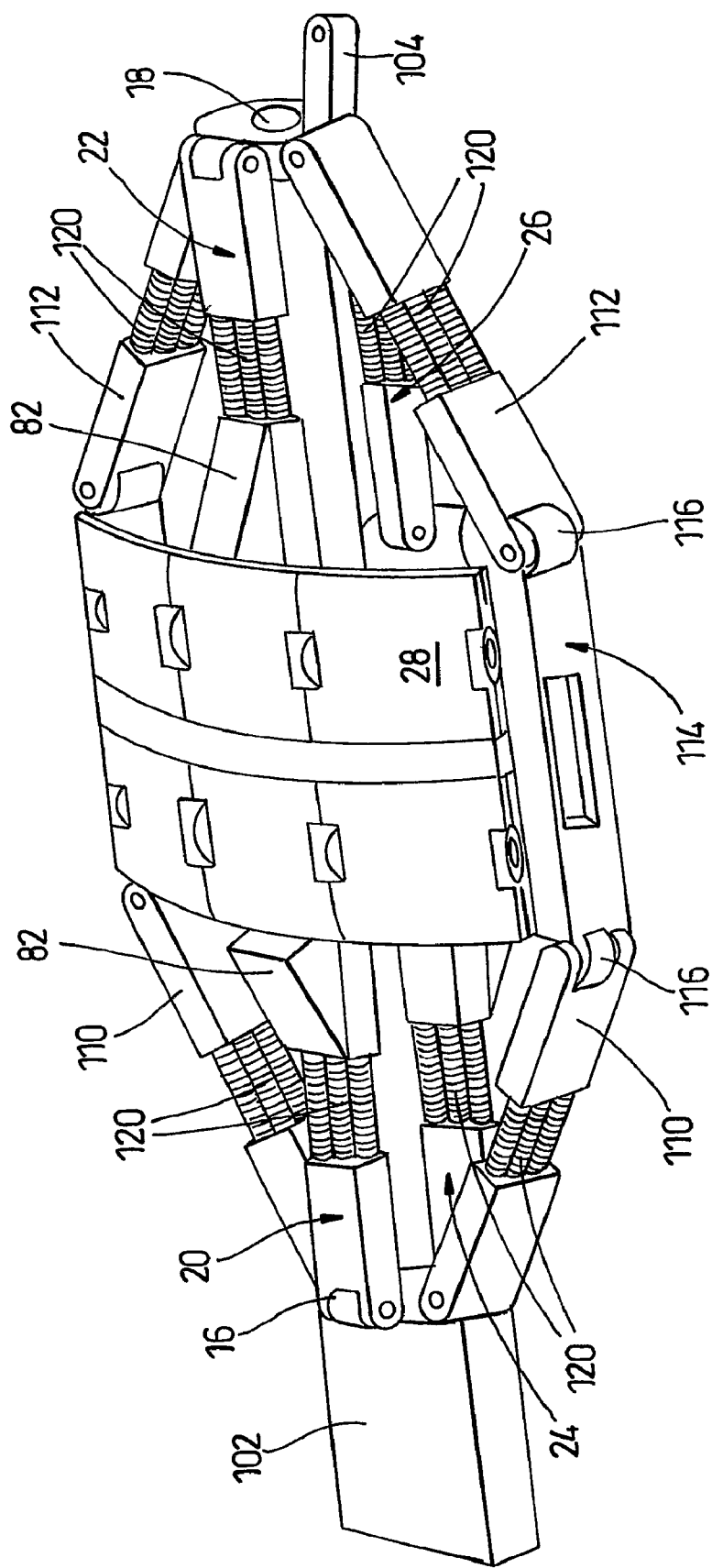
FIG. 8 shows the fourth embodiment of the present invention, in a second position.

A fourth embodiment of the present invention is illustrated in FIGS. 7 and 8. In this fourth embodiment, the centralising of the tool in the pipe is controlled by the same mechanism that controls the deployment of the inspection platforms. In this fourth embodiment, some components correspond to components of the earlier embodiments, and will be indicated by the same reference numerals.

Thus, the platforms 28, 30 are connected by a respective link arms 20 to 26 to brackets 16, 18. In this embodiment, the brackets 16, 18 are connected by a worm drive 100, powered by a drive motor 102. The motor 102 thus controls the separation of the brackets 16, 18 and hence the deployment and retraction of the platforms 28, 30. A towing connection 104 may be provided on the bracket 18.

In this fourth embodiment, the tool has a pair of centralising units 106, 108 each comprising first and second arms 110, 112 pivotally connected at one end to the respective brackets 16, 18 and at the other end pivotally connected to an axial link 114. Wheels 116 are provided at the junction of the axial links 114 and the arms 110, 112. In this arrangement, when the motor 102 drives the worm drive 100 to deploy or retract the platforms 28, 30, the resulting movement of the brackets 16, 18 also causes the centralising units 106, 108 to change shape, moving the axial link 114, and hence the wheels 116, towards or away from the worm drive 100. Thus, the wheels 116 are deployed and retracted in a similar way to the platforms 28, 30. Thus, the wheels 116 can be maintained in contact with the pipe, thereby centralising the worm drive 100 on the axis of the pipe, and hence ensuring that the platforms 28, 30 are in the correct position.

Preferably, the arms 110, 112 of the centralising units 106, 108 are of a length different from the link arms 20 to 26. This ensures that, in the retracted state, the wheels 116 and axial link 104 are outward of the inspection platforms 28, 30. This is illustrated in the retracted state illustrated in FIG. 8. This helps to guide the tool into e.g. a plug valve, and also provides additional protection for the platforms 28, 30.

FIGS. 7 and 8 also illustrate a further possible feature of the tool according to the present invention. As can be seen from FIGS. 7 and 8, each of the link arms 20 to 26, and each of the arms 110, 112 of the centralising units 106, 108 has a spring-section 120. The spring-section permits some variation in the length of the link arms 20 to 26 and the arms 110, 112 to provide compliance at bends and dents. Such a spring loading may be provided in the link arms, or centralising units, of the other embodiments.

Figure 9:
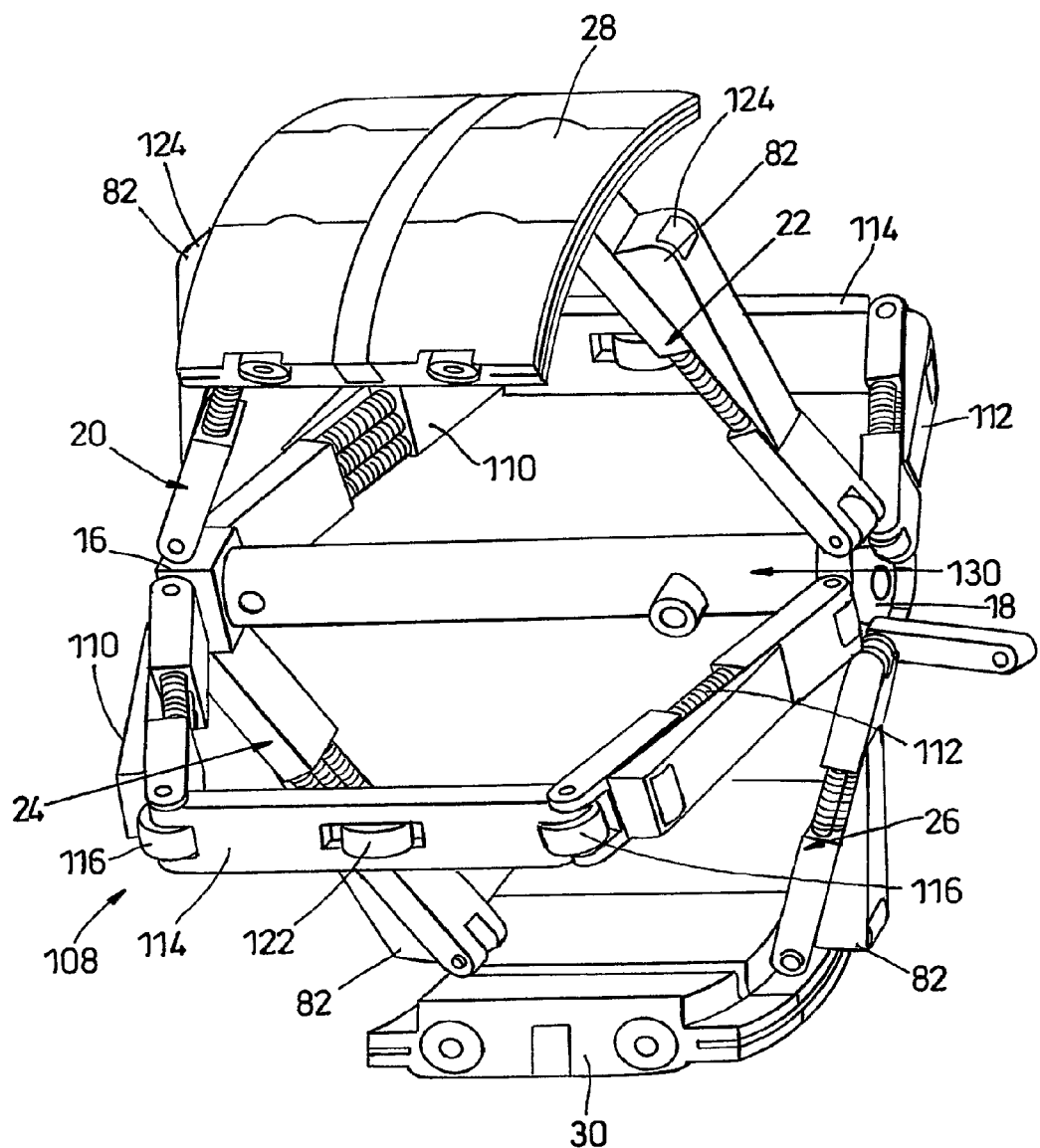
FIG. 9 shows a fifth embodiment of the present invention.

FIG. 9 illustrates a fifth embodiment of the present invention, which is generally similar to the fourth embodiment, and corresponding parts are indicated by the same reference numerals. However, in this fifth embodiment, the worm drive 100 and the motor 102 are replaced by a hydraulic ram 130. The advantage of this arrangement is that the overall axial length of the tool is shortened, by elimination of the projecting drive motor 102. The operation of this fifth embodiment is otherwise the same as the fourth embodiment, so it will not be described in more detail now.

Note, however, that in the embodiment of FIG. 9 the axial links 114 have a central wheel 122 therein, to provide further guidance, and rollers 124 are provided at the end of the deflectors 82 adjacent the platforms 28, 30.

As was mentioned previously, the inspection platforms 28, 30 permit inspection of the pipe by generating magnetic field which magnetise the pipe, with that magnetisation being detected by sensors in the platforms. The magnetisation is normally uniform, but defects, etc in pipe will affect the uniformity of the magnetisation, and hence can be detected by the sensors. The platforms 28, 30 will therefore now be described in more detail. In particular, each platform 28, 30 may comprise one or more platform units, referred to as magnetising shoes, each containing a pair of permanent magnets and corresponding sensors.

Figure 10:
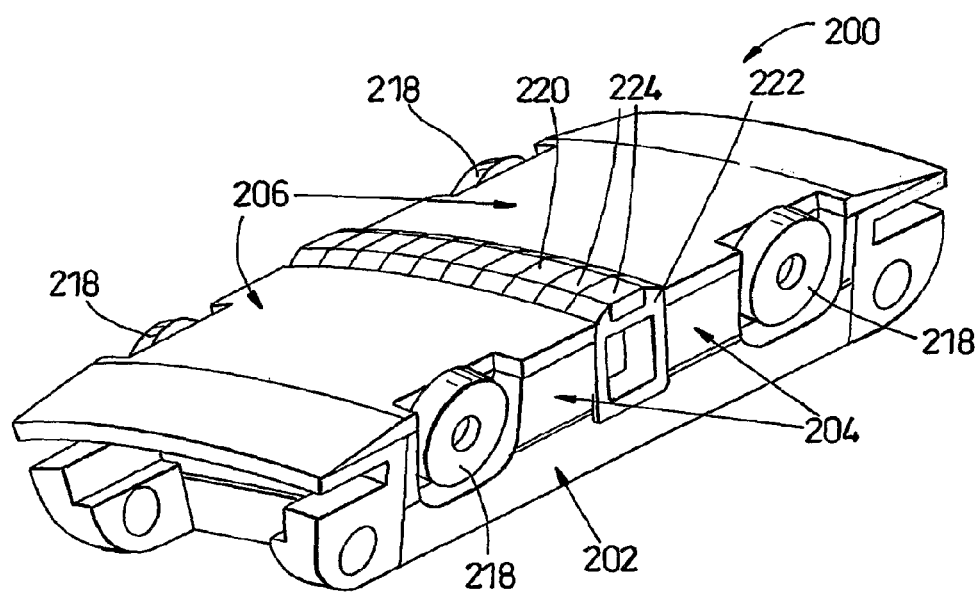
FIG. 10 shows an inspection platform shoe which may be used in any of the proceeding embodiments.

Thus referring to FIG. 10, a magnetising shoe 200 comprises a return path or magnet backing bar 202, a pair of enclosed permanent magnets 204 (also referred to as the "main magnets") and pole pieces 206. The main magnets 204 are magnetised in a direction corresponding to the thickness, with the main magnet at one end of the return path defined by the bar 202 being magnetised in the opposite direction to that on the other end.

Figure 11:
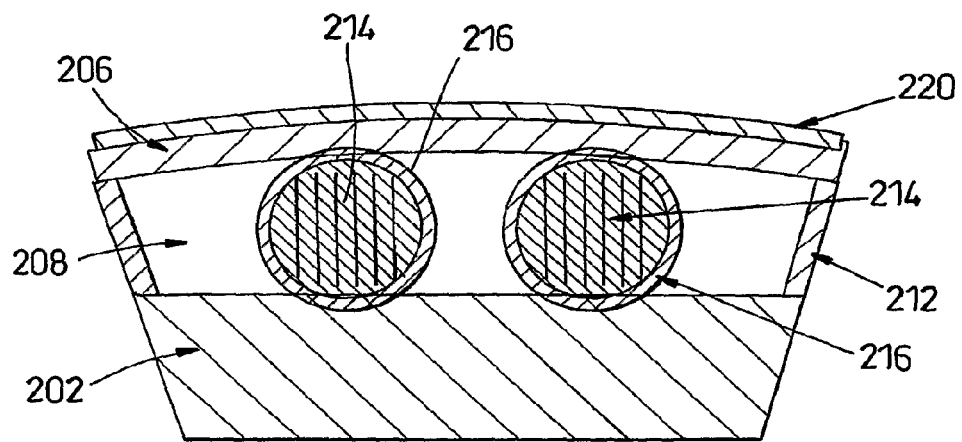
FIG. 11 is a sectional view through the shoe of FIG. 10.

Magnetic material is brittle, and therefore it is necessary to protect it within the shoe 200. Thus, as can be seen in FIG. 11, the magnetic material 208 of the permanent magnets 204 is mounted on the backing bar 202, is covered by a lid forming the pole piece 206 and has side cheeks 212. The brittle magnetic material is thus protected by the backing bar 202, the lid (pole piece 206) and the side cheeks 212.

The side cheeks 212 are fabricated from an austenitic stainless steel to prevent shorting of the permanent magnet material 208, whilst the lid (pole piece 206), backing bar 202 and pole piece 206 are fabricated from mild steel, or some other magnetic steel, to facilitate flux transference from the magnetic material 208.

The permanent magnets 204 are shaped to accommodate at least one (in this embodiment two) cylindrical magnets 214 (also referred to as a "magnetic shunt" or "shunt magnet") housed within a non-magnetic bearing or bush 216. The bush allows the cylindrical magnets 214 to rotate.

The cylindrical magnets 214 are magnetised across their diameters, and the direction of magnetisation is normally oriented parallel to that of the corresponding main magnet 206. The cylindrical magnets 214 are rotated by means of an actuator (not shown in FIGS. 10 and 11). A rotary actuator is preferred, but a linear actuator engaging with a spur, gearbox, or Geneva block to convert linear motion into rotary motion, may alternatively be used.

Wheels are mounted near the four corners of the magnetising shoe 200, and these contact and roll along the pipe wall during normal operation. The wheels 218 provide stability and a constant air gap between the pole pieces 206 and the pipe wall. This air gap means that there is no contacting friction between the magnetiser shoe and the pipe wall, considerably reducing the drag.

A rack 220 of sensors is mounted between the permanent magnets 204 and the pole pieces 206 of the magnetising shoe 200. The sensor rack 220 consists of a segmented flexible member 222, made of e.g. polyurethane, into each segment of which is mounted a corresponding electromagnetic sensor (not visible in FIG. 11) and a wear plate 224. The wear plate 224 contacts the pipe wall during inspection, and the polyurethane flexible member 222 provides local compliance over dents, weld beads etc. The output from the sensors are processed and recorded on an electronic data acquisition pack as part of the whole inspection system.

Figure 12:
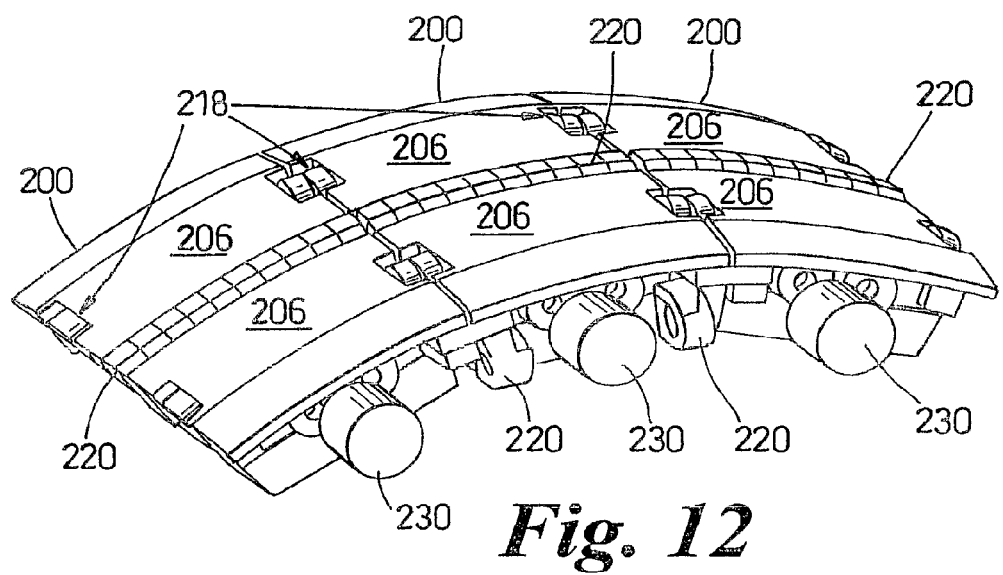
FIG. 12 shows an inspection platform incorporating inspection shoes corresponding to FIG. 10, which may be used in any of the first five embodiments.

Referring now to FIG. 12, preferably three or more magnetising shoes 200, more preferably an odd number, are attached together to form one of the inspection platforms 28, 30. An odd number is preferable as it allows the inspection platforms 28, 30 to be mounted through rotary pivots 226 on the central shoe 200 to e.g. the link arms 20 to 26, providing a balanced assembly. When combined in multiples, adjacent shoes 200 are connected via a flexible hinge or joint 228 shown in FIG. 13. This allows each magnetising shoe to flex inwards with respect to its neighbour, making it possible for the invention to conform to different pipe diameters.

As the pole piece is of fixed curvature, and the whole assembly is intended for use across a range of diameters, the radius of the pole is set to the smallest radius in the range. However the flexible joint 228 is set so that the overall curvature of the assembly is the same as that of the maximum diameter pipe. This ensures that the shoes 200 cannot flex upwards beyond the maximum diameter and preserves the minimum sensor pitch. For example, if the pipe range was from 400 to 500 mm, the pole piece 206 of an individual magnetising shoe 200 would have a radius of curvature of 200 mm. However, when combined with another two shoes as in FIGS. 12 and 13, the maximum overall radius without flexing would be 250 mm. This is the best compromise between geometry requirements and inspection requirements.

Figure 13:
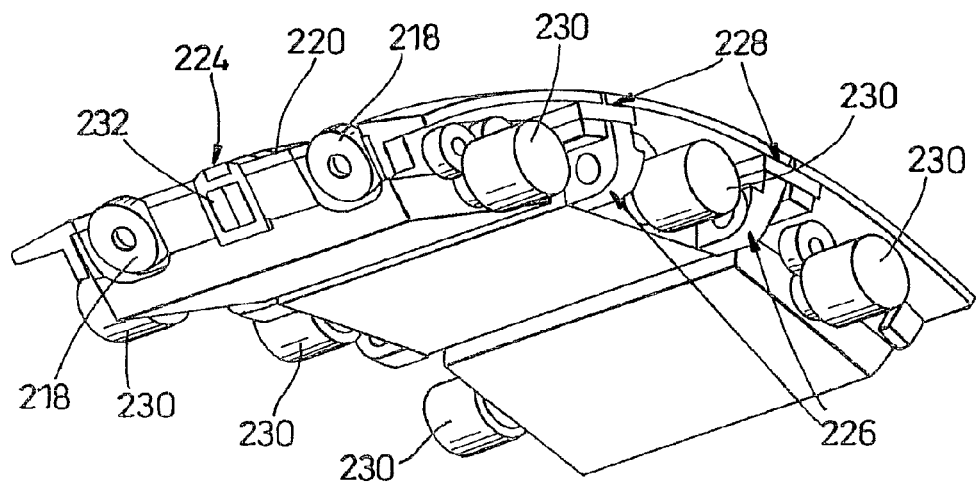
FIG. 13 is another view of the inspection platform of FIG. 12.

FIGS. 12 and 13 also illustrate the rotary actuators 230 which, as mentioned previously, rotate the cylindrical magnets 214. FIG. 13 also shows one sensor 232 at an end of the rack 220 of sensors.

Figure 14:
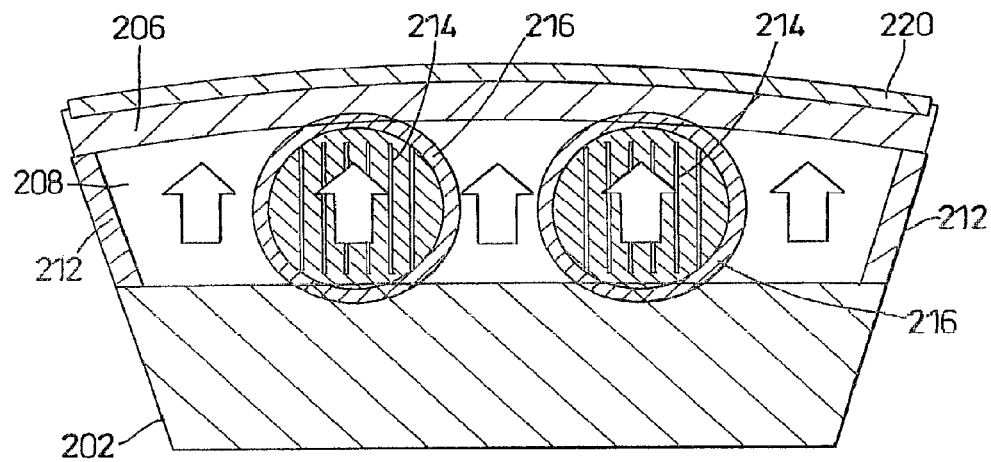
FIG. 14 is a view similar to FIG. 11, but showing one possible direction for magnetic fields.
Figure 15:
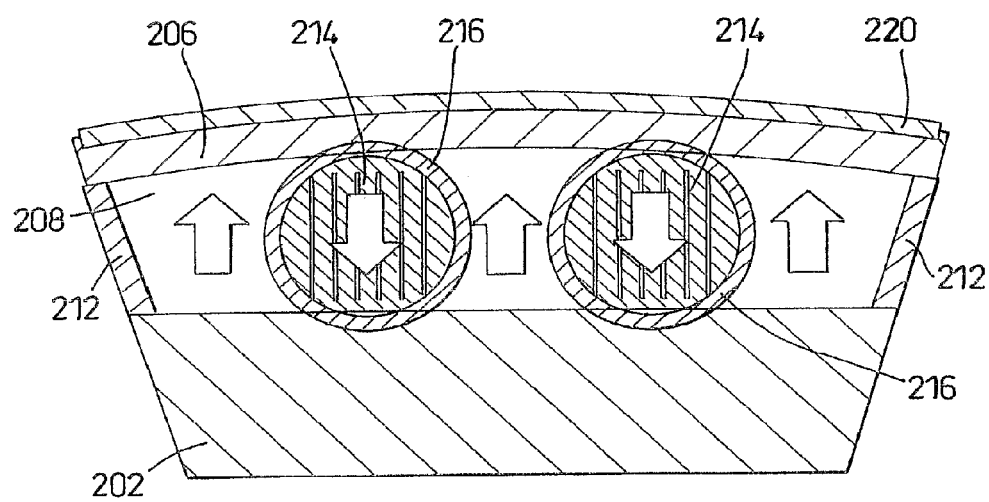
FIG. 15 is a view similar to FIG. 14, but showing a different arrangement for magnetic fields.
Figure 16:
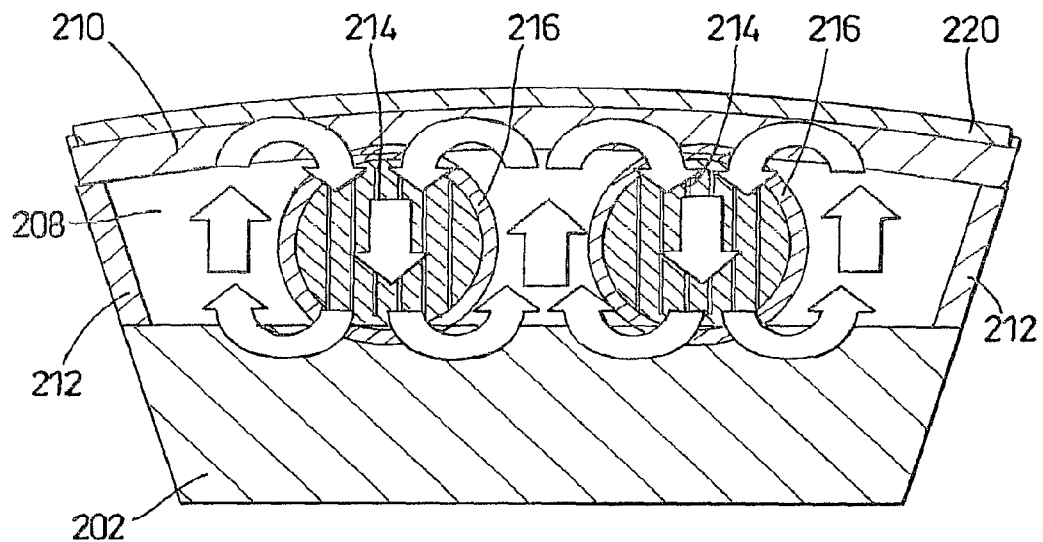
FIG. 16 shows magnetic flux paths in the configuration of FIG. 15.

During normal operation (i.e. when the inspection platform 28, 30 are deployed to inspect the internal wall of the pipe, the cylindrical shunt magnets 214 are driven by the actuators 230 so that their magnetic fields are aligned with the magnetic fields of the surrounding magnetic material 208. This is illustrated in FIG. 14. The result is that the magnetic flux generated by the shunt magnets 214 adds to the magnetic flux generated by the magnetic material 208, so that the magnetic field generated by the corresponding permanent magnet 204 is large. Thus, the pole pieces will magnetise the adjacent pipe wall. When it is not intended to inspect the pipe wall, or e.g. when the inspection of platforms of 28, 30 are retracted in the embodiments illustrated in FIGS. 2 to 9, it is desirable to reduce the magnetic field generated by the permanent magnets 204. Therefore, the actuators 230 are driven to rotate the shunt magnets 214, until their magnetic fields are in anti-parallel to the magnetic fields of the permanent magnet 208. This is illustrated in FIGS. 15 and 16. The direction of the magnetisation of the shunt magnets 214 is thus 180° to the main field, and so they have a negative contribution to the field generated by the permanent magnets 204. The magnetic flux thus has a tendency to flow in closed loops within the permanent magnets 204, as illustrated in FIG. 16, rather than exiting through the pole piece 206 and into the pipe wall.

The result is a reduction in the magnetic field generated at the pole pieces 206, thereby reducing the magnetic attraction between the shoe 200 and the wall of the pipe. The magnitude of this effect is a function of the relative sizes and strengths of the permanent magnet material 208 and the shunt magnets 214, and also the thickness of the backing bar 202 and the pole piece 206. Depending on the size of the shunt magnets relative to the magnetic material 208, which is also dependent on the size of the shoe 200, it is possible to give partial field reduction or almost total field cancellation.

Thus, if the inspection platforms 28, 30 of the embodiments of FIGS. 1 to 9 are formed of shoes as illustrated in the embodiments of FIGS. 10 to 16, the resulting tool can have the positions of the inspection platforms varied, and also the strength of the magnetic field generated by those platforms be varied. The tool can thus be conformed to a wide variation in pipe configurations, permitting inspection of pipes which could not be inspected by standard pipeline pigs.

Figure 17:
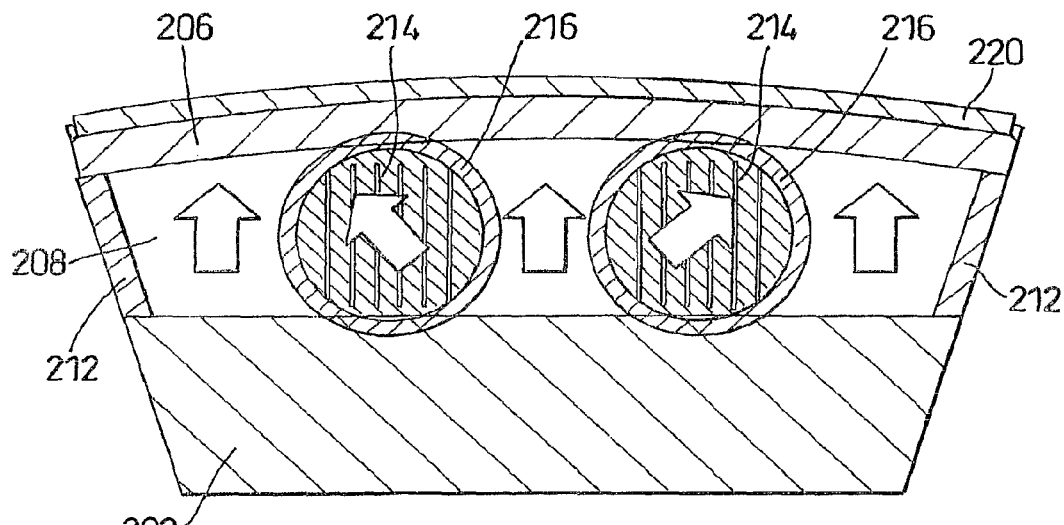
FIG. 17 is similar to FIGS. 14 and 15 but shows another possible arrangement for magnetic fields.

In the arrangement discussed with reference to FIGS. 10 to 16, and in particular FIGS. 14 and 15, the direction of the magnetisation of the shunt magnets 214 is either in parallel (FIG. 14) or anti-parallel (FIG. 15) to the magnetic flux generated by the magnetic material 208. However, it is also possible to have the magnetisation of the shunt magnets 214 at some other angle to the magnetic field generated by the magnetic material 208. An example of this is illustrated in FIG. 17, where the shunt magnets 214 are positioned so that their magnetisation is inclined at approximately 45° to the magnetic flux generated by the magnetic material 208. Apart from the orientation of the shunt magnets 214, the arrangements of FIG. 17 is the same as that of FIGS. 14 and 15 and the same reference numerals are used to indicate corresponding parts. Note that, in FIG. 17, although the magnetisation of the shunt magnets 214 are inclined, the inclination of the two shunt magnets 214 are in opposite directions.

By inclining the shunt magnets 214 as shown in FIG. 17, the total magnetic field generated by the permanent magnet 204 is reduced, as compared with the arrangement shown in FIG. 14. Thus, by inclining the shunt magnets 214 at an appropriate angle, the maximum magnetic field can be controlled. Such control is useful where the pipeline pig is to be used in pipes of varying wall thickness. As previously mentioned, the field generated in a thin walled pipe will be higher than that in a thicker walled pipe, and thus the generation of fields which are not the maximum possible (as they are in FIG. 14) becomes desirable in order to reduce the magnetic field in a thin walled pipe for a suitable value. This can enable prevention of saturation or "clipping" of the signals in the electronics processing the outputs of the sensors, to prevent hysteresis effects, and also to obtain data at fields for which the pipe wall is not saturated. The shunt magnets 214 can be rotated to any suitable angle, thereby to adjust the overall field to that which is desired.

The invention claimed is:

1. An inspection platform for an in-line pipe inspection tool, comprising:
    a curved body having one or more permanent magnets defining north and south poles and arranged circumferentially relative to a direction of motion of the in-line pipe inspection tool along the pipe;
    sensors mounted between those poles; and
    a rotatable magnet provided within the one or more permanent magnets.

2. An inspection platform according to claim 1, having a pair of said permanent magnets, either or each of which contains a rotatable magnet, and said sensors are in a sensor array between said pair of permanent magnets.

3. An inspection platform according to claim 1, comprising a plurality of platform units, each having one or more permanent magnets defining north and south poles, sensors mounted between the poles, and at least one rotatable magnet within the permanent magnet.

4. An inspection platform according to claim 3, wherein the platform units are connected by a flexible joint.

5. An inspection platform according to claim 1, wherein the rotatable magnet is cylindrical, and the rotatable magnet is mounted in a bore in the one or more permanent magnets.

6. An inspection platform according to claim 1, further comprising:
    a bush provided in a bore of the permanent magnet and configured to accommodate the rotatable magnet.

7. An inspection platform according to claim 1, further comprising:
    one or more wheels attached to the curved body and configured to contact a wall pipe when the inspection platform is provided inside the pipe.

8. An inspection platform according to claim 7, wherein the one or more wheels are configured to provide a constant gap between the inspection platform and a pipe wall.

9. An inspection platform according to claim 1, further comprising:
    a pole piece configured to cover the permanent magnet.

10. An inspection platform according to claim 1, further comprising:
    another permanent magnet;
    a segmented flexible member provided between the at least one permanent magnet and the another permanent magnet, wherein the segmented flexible member is configured to receive the sensors; and
    a wear plate configured to cover the sensors.

11. An inspection platform according to claim 10, wherein the flexible member is elastic to provide local compliance over non-uniform surfaces in a pipe wall.

12. An inspection platform according to claim 1, further comprising:
   an actuator configured to rotate the rotatable magnet.

13. An inspection platform for an in-line pipe inspection tool, the inspection platform comprising:
   a body configured to have a curvature substantially perpendicular to a direction of motion of the in-line pipe inspection tool along the pipe;
   a permanent magnet provided on the body along the curvature and defining north and south poles; and
   a rotatable magnet provided inside a bore of the permanent magnet and configured to rotate relative to the permanent magnet.

14. The inspection platform according to claim 13, further comprising:
   a bush provided in the bore of the permanent magnet and configured to accommodate the rotatable magnet.

15. The inspection platform according to claim 13, further comprising:
   a pole piece configured to cover the permanent magnet to protect if from a pipe wall.

16. The inspection platform according to claim 13, further comprising:
   another permanent magnet;
   a segmented flexible member provided between the permanent magnet and the another permanent magnet, wherein the segmented flexible member is configured to receive at least one sensor; and
   a wear plate configured to cover the at least one sensor.

17. The inspection platform according to claim 16, wherein the flexible member is elastic to provide local compliance over non-uniform surfaces in a pipe wall.

18. An inspection platform for an in-line pipe inspection tool, the inspection platform comprising:
   a body configured to have a curvature substantially perpendicular to a direction of motion of the in-line pipe inspection tool along the pipe;
   a permanent magnet provided on the body along the curvature and defining north and south poles;
   a rotatable magnet provided inside a bore of the permanent magnet and configured to rotate relative to the permanent magnet; and
   an actuator configured to rotate the rotatable magnet.

19. The inspection platform according to claim 18, further comprising:
   a bush provided in the bore of the permanent magnet and configured to accommodate the rotatable magnet.

20. The inspection platform according to claim 18, further comprising:
   a flexible member provided next to the permanent magnet, wherein the flexible member is configured to receive at least one sensor; and
   a wear plate configured to cover the at least one sensor.

* * * * *